United States Patent [19]

Spaeth et al.

[11] Patent Number: 5,354,303
[45] Date of Patent: Oct. 11, 1994

[54] DEVICES FOR ENCLOSING, MANIPULATING, DEBULKING AND REMOVING TISSUE THROUGH MINIMAL INCISIONS

[75] Inventors: Edmund E. Spaeth, Orange; Alexander S. Borsanyi, Newport Beach; Alex Bowie, Irvine; John T. Sorensen, Costa Mesa, all of Calif.

[73] Assignee: EndoMedix Corporation, Irvine, Calif.

[21] Appl. No.: 836,087

[22] Filed: Feb. 14, 1992

Related U.S. Application Data

[63] Continuation-in-part of Ser. No. 639,494, Jan. 9, 1991, abandoned, and a continuation-in-part of Ser. No. 779,443, Oct. 18, 1991.

[51] Int. Cl.$^5$ .............................................. A61B 17/22
[52] U.S. Cl. ................... 606/128; 606/113; 606/114; 606/127; 604/27; 604/171; 604/172
[58] Field of Search ................ 606/1, 110, 113, 114, 606/127, 128; 600/37; 604/27, 171, 172, 318; 128/749

[56] References Cited

U.S. PATENT DOCUMENTS

| 15,477 | 3/1874 | Bradford . | |
|---|---|---|---|
| 30,471 | 10/1860 | Dudley . | |
| 1,609,014 | 9/1925 | Dowd . | |
| 4,557,255 | 12/1985 | Goodman . | |
| 4,997,435 | 3/1991 | Demeter | 606/127 |
| 5,037,379 | 8/1991 | Clayman et al. | 604/27 |
| 5,143,082 | 9/1992 | Kindberg et al. | 128/749 |
| 5,147,371 | 9/1992 | Washington et al. | 606/110 |
| 5,176,687 | 1/1993 | Hasson et al. | 606/114 |
| 5,190,542 | 3/1993 | Nakao et al. | 606/1 |
| 5,190,555 | 3/1993 | Wefer et al. | 606/1 |
| 5,190,561 | 3/1993 | Graber | 606/114 |
| 5,192,284 | 3/1993 | Pleatman | 606/110 |
| 5,192,286 | 3/1993 | Phan et al. | 606/127 |

OTHER PUBLICATIONS

DE 3029-064 (Abstract Only).
DE 3522-649 (Abstract Only).
DE 3626-371 (Abstract Only).
DE 3603-344 (Abstract Only).
DE 3717-658 (Abstract Only).
DE 3913-936 (Abstract Only).
EP 27 ∝ 704 (Abstract Only).
EP 123175 (Abstract Only).
EP 156202 (Abstract Only).
GB 2 020 557 (Abstract Only).
WO 91/02493 (Abstract Only).
WO 91/03983 (Abstract Only).
Booklet: Phillips, E. H., Laparoscopic Cholecystectomy With Common Bile Duct Exploration, Johnson & Johnson Corporation; Ethicon Division.
Booklet: Partain, N., Laparoscopic Surgery and the O. R. Nurse, Johnson & Johnson Corporation; Ethicon Division.

Primary Examiner—William E. Kamm
Assistant Examiner—Brian L. Casler

[57] ABSTRACT

Containment sacs insertable into a body cavity through a minimal access incision for purposes of containing, manipulating, treating and/or extracting material from the body cavity. The sac may comprise a flexible sac body having at least one opening thereinto and a resilient or spring loaded rim member disposed about the opening to urge the opening to an open configuration when deployed in the body cavity. The containment sac may be further utilized in combination with a dedicated introducer sheath through which the containment sac may be inserted and extracted. A valving member may be positioned on the introducer sheath to prevent escape of gas from a pressurized body cavity such as a pneumoperitoneal. The containment sac may incorporate a grasping member whereby the containment sac may be grasped and inserted using a standard forcep/grasper instrument. Alternatively, the containment sac may be attached to an elongate rod member usable to insert and extract the containment sac. Additionally disclosed is an expandable embodiment of the containment sac which may be selectively expanded through the use of a separate expansion instrument or balloon.

59 Claims, 6 Drawing Sheets

DEVICES FOR ENCLOSING, MANIPULATING, DEBULKING AND REMOVING TISSUE THROUGH MINIMAL INCISIONS

RELATED INVENTIONS

The subject application is a continuation-in-part of U.S. patent application Ser. No. 07/639,494, filed on Jan. 9, 1991 now abandoned, entitled METHOD AND DEVICE FOR INTRACORPOREAL LIQUIDIZATION OF TISSUE AND/OR INTRACORPOREAL FRAGMENTATION OF CALCULI DURING ENDOSCOPIC SURGICAL PROCEDURES, and U.S. patent application Ser. No. 07/779,443, filed on Oct.18, 1991, entitled METHOD AND SYSTEM FOR ENCLOSING, MANIPULATING, DEBULKING AND REMOVING TISSUE THROUGH MINIMAL ACCESS INCISIONS.

FIELD OF THE INVENTION

This invention relates generally to medical equipment and, more particularly to a methods and devices whereby a flexible containment sac or bag is inserted into a body cavity, for containment and morcellization of excised tissue or matter, and to facilitate subsequent removal of such tissue or matter from the body cavity through a relatively small incision.

INCORPORATION BY REFERENCE

The entire disclosure of U.S. patent application Ser. Nos. 07/639,494, filed on Jan. 9, 1991, and 7/779,443, filed on Oct. 18, 1991 are hereby incorporated by reference.

BACKGROUND OF THE INVENTION

The advent of modern endoscopic surgical procedures (e.g. laparoscopic procedures) has enabled the performance of complex excisional surgery through minimal access incisions of approximately 1 centimeter. Such procedures may be utilized to excise or resect relatively large volumes of tissue, tumors, organs and the like. The extraction and removal of such excised tissues, tumors, organs or the like is, however, sometimes problematic because such excised tissue, tumors, organs or the like are often too large or bulky to be removed directly through the minimal access (e.g. 1 cm) endoscopic incision. Also, the excision, manipulation and removal of certain non-benign matter (e.g. infected tissue, fecally contaminated segments of bowel, cancerous tumors) is complicated by the need to contain such non-benign matter in a manner that will prevent or deter dissemination or spread of such non-benign matter within the body cavity.

Accordingly, there exists a need in the art for new appliances and apparatus for containing, manipulating, morsellizing or debulking, and/or removing excised tissues, tumors, organs or other matter, through relatively small minimal access incisions.

A surgical tissue bag and method for percutaneously debulking tissue is purportedly described in U. S. Pat. No. 5,037,379 (Clayman et al.).

A surgical tissue sac for use in endoscopic surgical procedures is presently available commercially under the name ENDOPOUCH ™ (Ethicon, Inc., Division of Johnson & Johnson, Route 22, P. 0. Box 151, Somerville, N.J. 08876).

The surgical tissue containment sacs of the prior art may present certain shortcomings in that such prior devices (a) lack optimally efficient and/or safe means for inserting/retracting in the containment sac, (b) do not adequately open or fully expand the containment sac when inserted into a body cavity through a minimal access incision, (c) lack means for maintaining directional orientation of the bag opening during intracorporeal usage, (d) lack sufficient transparency to permit ease of viewing through the wall of the containment sac and/or (e) lack means for facilitating passage of instruments into the containment sac for purposes of treating, grinding, debulking or removing material from the interior of the sac.

SUMMARY OF THE INVENTION

The present invention comprises a containment sac device which is insertable into and/or extractable from a body cavity through a minimal access incision.

In accordance with the invention, there is provided one embodiment of a containment sac device comprising a flexible containment sac having at least one grasping member formed thereon. Such grasping member is sized and configured to be grasped by a standard laparoscopy forcep/grasper instrument.

A resilient or spring loaded rim member may be disposed about the opening of the containment sac to urge the containment sac to an open configuration when it is inserted into a desired body cavity.

Further in accordance with the invention, the containment sac device may incorporate a dedicated introducer comprising a tubular sheath through which the containment sac may be inserted and/or extracted. An elastomeric cap/valving member may be positioned on the proximal end of such tubular introducer to prevent leakage of pressure from a pressurized body cavity (e.g., a pneumoperatenium) during operative use.

Further in accordance with the invention, there is provided an embodiment of a containment sac device which comprises (a) a flexible containment sac having at least one opening formed therein, (b) a hinged rim member disposed about the opening of said containment sac. An elongate plunger member may be attached to said rim member to facilitate insertion and extraction of the containment sac through a trocar or tubular introducer sheath.

Still further in accordance with the invention, the containment sacs may be formed of transparent material to facilitate endoscopic visualization of material within the containment sac. Next, still further in accordance with the invention, all or a portion of the containment sac body may be reinforced with fibers, plastic strips, expandable metal foils or other reinforcement means all or portions of the containment sac body.

Still further in accordance with the invention, there is provided an embodiment of a containment sac device wherein at least a portion of the containment sac body is selectively expandable by way of an expansion tool or balloon.

Additional objects and advantages of the invention will be apparent to those skilled in the art upon reading and understanding of the accompanying detailed descriptions and drawings.

BRIEF DESCRIPTION OF THE DRAWINGS

FIG. 6 is a perspective view of a spring biased rim member positionable within the containment sac portion of the device of the present invention;

FIG. 6a is a perspective view of the portion of the rim member of FIG. 6 within line 6a—6a;

FIG. 6b is an exploded view of the portion of the rim member of FIG. 6 denoted by line 6b—6b;

FIG. 6c is a partial cut-away view of the portion of the rim member of FIG. 6 denoted by line 6c—6c;

FIG. 7 is a partial perspective view of an alternative tab section of the rim member wherein the free ends of the wire are conjoined by twisting;

FIG. 12a is a perspective view of one embodiment of the containment sac portion of a device of the present invention;

FIG. 12b is a side elevational view of the containment sac shown in FIG. 12a;

FIG. 12c is a perspective view of an alternative configuration of the containment sac portion of a device of the present invention;

FIG. 12d is a perspective view of another alternative configuration of the containment sac portion of a device of the present invention;

DETAILED DESCRIPTION OF A PREFERRED EMBODIMENT

A. The Device of The Present Invention

The following detailed description and the accompanying drawings are provided for purposes of describing and illustrating specific embodiments of the invention only and are not intended to describe the only embodiments in which the invention may exist, or to limit the scope of the invention in any way.

The containment sacs of the present invention may be inserted into and/or extracted from a body cavity through any suitable incision, tubular trocar or portal. Indeed, the containment sacs of the present invention may need not be provided with their own tubular introducer sheaths. Rather, the containment sacs of the present invention may be independently inserted and extracted through any routinely used type of laparoscopy, trocar or portal. Nonetheless, the preferred embodiment of the device described herein incorporates a dedicated introducer sheath which may be slideably advanced through a standard laparoscopy trocar or portal for the purpose of facilitating insertion/extraction of the containment sac device. The provision of such dedicated introducer sheath is an optional feature of the invention.

Referring to the drawings, there is shown a presently preferred device of the present invention as utilized in conjunction with a standard laparoscopy forcep/grasper instrument.

Figures 1, 2, 2A, 3, 4, 5, 5A:
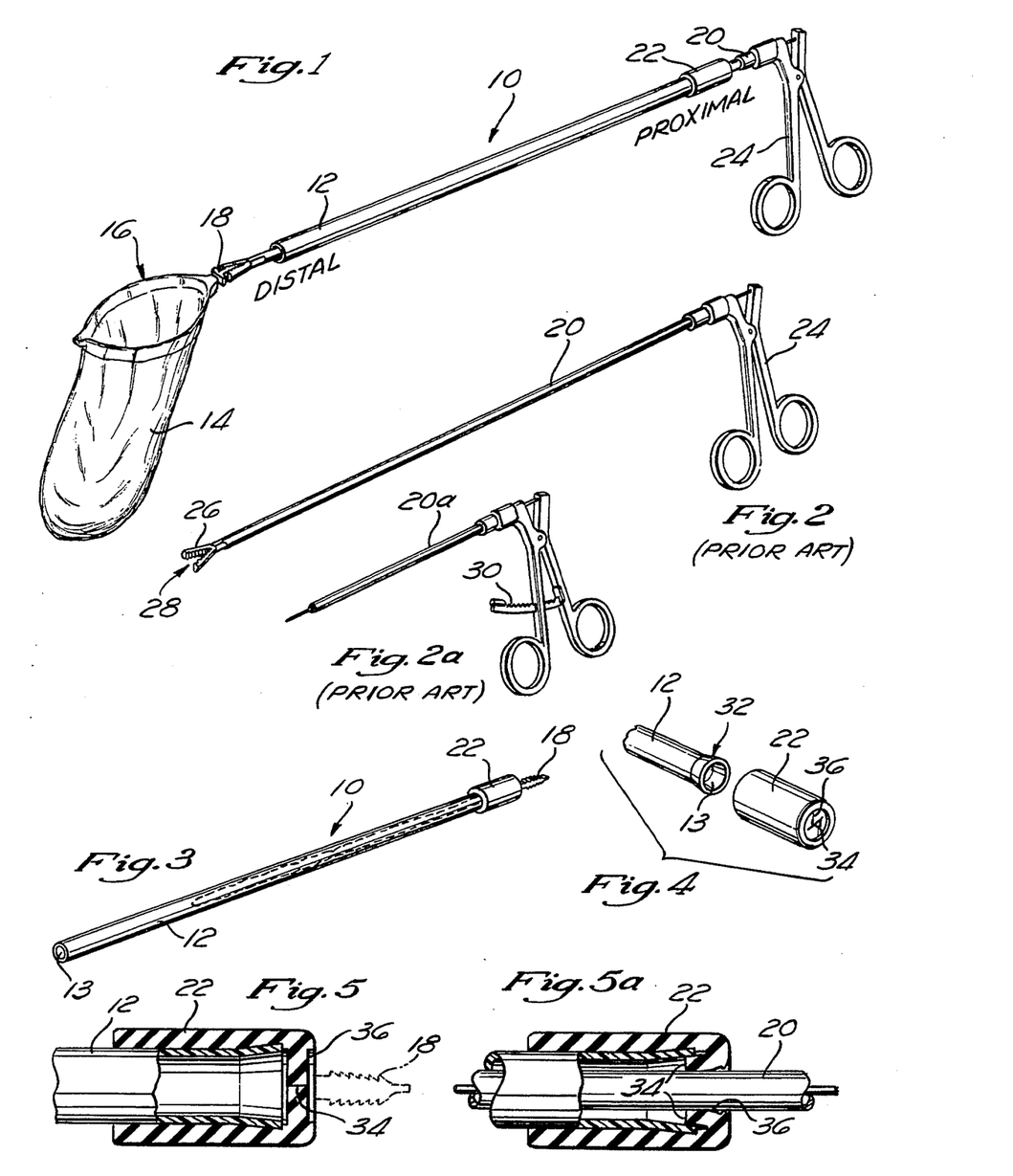
FIG. 1 is a perspective view of an embodiment of a device of the present invention having a standard laparoscopy forcep/grasper instrument operatively inserted therethrough and thereon.
FIG. 2 is a perspective view of a standard laparoscopy forcep/grasper instrument of the prior art.
FIG. 2a is a partial perspective view of the proximal hand-held portion of a standard laparoscopy forcep/grasper instrument of the prior art incorporating an optional releasable locking apparatus.
FIG. 3 is a perspective view of an embodiment of the device of the present invention disposed in a pre-operative configuration wherein the containment sac is contained within the lumen of introducer sheath.
FIG. 4 is an exploded view of the proximal portion of a device of the present invention showing (i) the proximal end of the tubular introducer sheath and (ii) an elastomeric cap/valving member positionable on the proximal end of the introducer sheath.
FIG. 5 is a partial longitudinal sectional view of the proximal end of a device of the present invention disposed in its pre-operative configuration.
FIG. 5a is a partial longitudinal sectional view of the proximal end of a device of the present invention disposed in its operative configuration with the shaft of a standard laparoscopy forcep/gripper instrument inserted therethrough.

Specifically, the device 10 comprises an elongate tubular introducer sheath 12 having a distal end and a proximal end as shown. A hollow bore or lumen 13 extends longitudinally through the introducer sheath 12. An elastomeric cap/valving member 22 is positioned on the proximal end of the introducer sheath 12. Such elastomeric cap/valving member 22 is generally cylindrical in configuration and is sized to fit snugly over the proximal end of the introducer sheath 12. The proximal end of the introducer sheath may be slightly flared, as shown in FIG. 4, to increase frictional retention of the cap/valving member 22 thereon. A transverse elastomeric seal or diaphragm 36 is formed on the proximal end of the cap/valving member 22. A slit 34 is formed in the elastomeric diaphragm 36 of cap/valving member 22, as shown in FIG. 4. Such slit 34 is biased to a closed configuration to form a substantially gas-tight seal, thereby deterring or preventing loss of positive pressure from the pneumoperitoneum when the introducer sheath 12 is inserted thereinto. The slit 34 is further sized and configured to permit the shaft portion of a standard laparoscopy forcep/grasper instrument 20 to be inserted and advanced therethrough with the slit 34 forming a substantially gas-tight seal around the shaft portion of the laparoscopy forcep/trocar instrument 20. When so inserted, the instrument 20 remains slidably advanceable, rotatable, and retractable through the slit 34. The embodiment of the device 10 shown in FIGS. 1–11 further comprises a containment sac 14. Two (2) possible configurations of the containment sac 14 are shown in FIGS. 12a–12d. The containment sac 14 comprises a flexible sac body 15 having at least one top opening or mouth formed therein. A rigid or semi-rigid rim member 16 disposed about and/or attached to the top opening of the sac body 15. As described more fully herein, the rim member 16 is preferably biased to an "open" configuration whereby the rim member 16 will urge the top opening or mouth of one sac body 15 to an open configuration so as to facilitate insertion of tissue or other matter into the containment sac 14.

Prior to operation of the device 10, the containment sac 14 is disposed in a "preoperative" position. In such "pre-operative" position, the containment sac 14 is fully contained within the hollow lumen 13 of the introducer sheath 12. A grasping member 18, attached to the rim of the containment sac 14, protrudes out of and beyond the proximal end of the introducer sheath 12 so as to minimally deform the slit 34 of the cap/valving member 22 and to be readily graspable by a standard forcep/grasper instrument 20.

The containment sac 14 may be initially disposed in the above-described "pre-operative" position at the point of manufacture and subsequently shipped and stored in such "pre-operative" position until its time of use during surgery. Alternatively, the containment sac 14 may be packaged and/or shipped separately from the introducer sheath 12 and the containment sac 14 may be pre-loaded into the introducer sheath 12 immediately before use during surgery.

With the containment sac 14 disposed in such "pre-operative" position, the introducer sheath 12 is readily inserted, distal end first, through a small incision and into a body cavity such as the abdominal cavity. The diameter of the introducer sheath 12 is preferably 1 cm or less to permit the introducer sheath 12 to pass through a minimal access incision of approximately 1 cm length. Typically, a laparoscopy trocar, portal, or other insertion-facilitating apparatus will have been pre-inserted into the minimal access incision prior to passage of the introducer sheath 12 therethrough.

After the distal end of the introducer sheath 12 has been inserted into the body cavity, a standard laparoscopy forcep/grasper instrument 20 may be utilized to grasp grasping member 18 and to push the containment sac 14 out of the distal end of the introducer sheath 12. The containment sac 14 will then assume the "deployed" configuration shown in FIG. 1.

Samples of forcep/grasper instruments which may be utilized for this purpose are the ENDOPATH ® Grasper and ENDOPATH ® Locking Grasper available commercially from Ethicon, Inc., Division of Johnson & Johnson, Route 22, P.O. Box 151, Somerville, N.J. 08876.

As the containment sac 14 passes out of the distal end of the introducer sheath 12 to its "deployed" configuration, the outwardly biased rim member 16 will automatically cause the top opening or mouth of the sac body 15 to assume an open configuration. Thereafter, the jaws 26 of the forcep/grasping instrument 20 may be disengaged from the grasping member 18, thereby rendering the containment sac 14 fully released and free to move about within the body cavity.

Separate instruments inserted through secondary portals may then be utilized to guide and manipulate the containment sac 14 to a desired position within the body cavity whereat the desired organ, tissue or other matter may be deposited into the containment sac 14. Thereafter, the separate instruments are utilized to return the containment sac 14 to a position near the distal end of the introducer sheath such that the forcep/grasper instrument may be once again utilized to grasp grasping member 18 and to withdraw a portion of the containment sac 14 into the lumen 13 of the introducer sheath 12.

The grasping member 18 attached to the containment sac 14 comprises a rigid body having a plurality of serrated teeth 28 formed thereon. The serrated teeth 28 formed on the gripping member 18 are preferably sized, spaced and configured to correspond to similar serrated teeth 28 formed on the jaws 26 of the forcep/grasper instrument 20 such that the jaws 26 of the instrument 20 may be utilized to firmly grasp the grasping member 18.

Figures 8, 9, 10, 11:
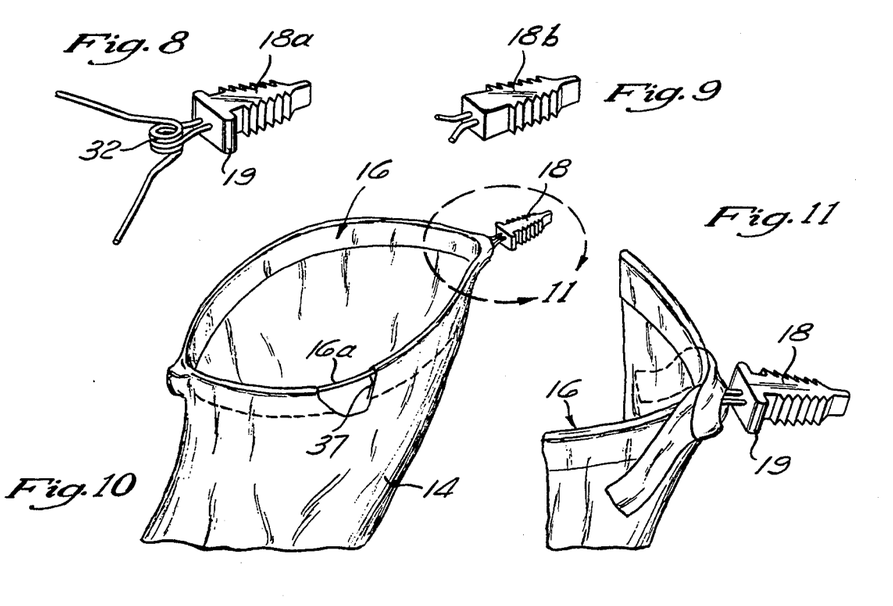
FIG. 8 is a perspective view of a first embodiment of a gripping member (tab) attachable to the rim member portion of a containment sac of the present invention.
FIG. 9 is a perspective view of an alternative embodiment of a gripping member attachable to the containment sac portion of a device of the present invention.
FIG. 10 is a partial perspective view of the containment sac portion of a device of the present invention.
FIG. 11 is a cut-away perspective view of the containment sac portion of a device of the present invention incorporating a reinforcement tape member disposed thereon.

The grasping member 18 may be provided with a frontal flange member 19 as shown in FIG. 8. Such frontal flange member will serve as an abutment block against which the frontal tips of the jaws 26 of the forcep/grasper instrument 20 may abut, thereby facilitating optimal positioning of the grasper instrument jaws 26 on the grasping member 18a. In an alternative embodiment, shown in FIG. 9, the grasping member 18b may be formed without a frontal abutment flange 19.

The optional frontal abutment flange 19 may be specifically sized and configured to perform the dual functions of (a) preventing the jaws 26 of the forcep/grasper instrument 20 from passing in a proximal direction beyond the front of the grasping member 18 as my result in perforation of the containment sac, and (b) preventing the jaws 26 of the grasper from being positioned too far forward on the angular body of the grasping member 18 as may result in excessive splaying of the jaws 26 with the resultant inability to fully open and disconnect the jaws 26 from the grasping member 18 when positioned and confined within the lumen 13 of the introducer sheath 12.

Figures 6, 6A, 6B, 6C, 7:
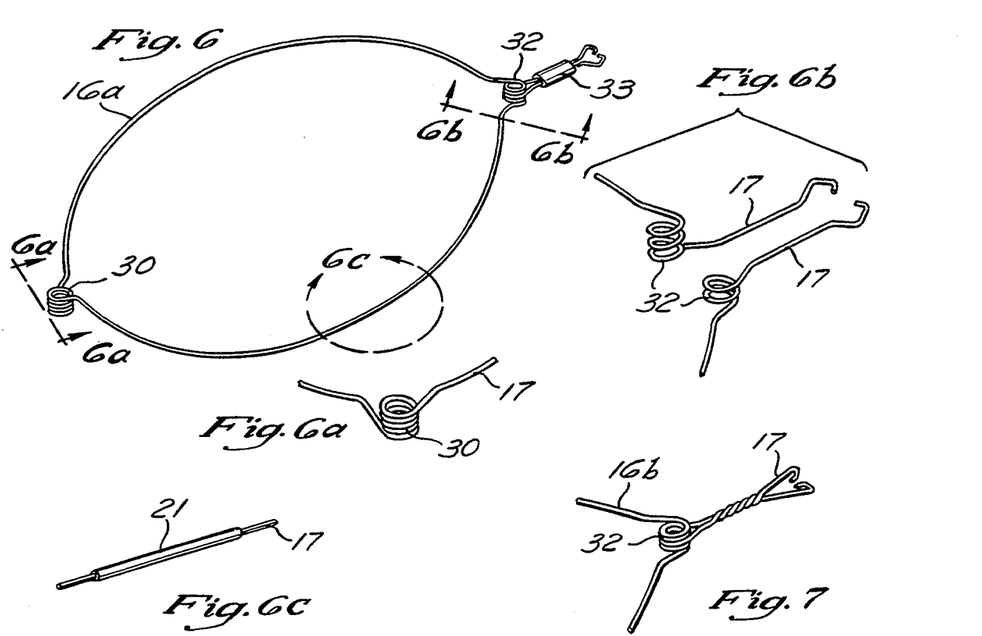

It will be appreciated that various types of resilient or spring-loaded rim members may be positioned within the rim of the containment sac 14 so as to bias the containment sac 14 to an open configuration. One presently preferred rim member 16a is shown in FIGS. 6–6c. As shown, this presently preferred rim member 16a comprises a loop of spring metal wire having a front coil 30 and a rear coil 32 formed therein. The front 30 and rear 32 coils of this preferred embodiment each consist of five (5) loops of wire, although coils having greater than 5 or less than 5 loops may be utilized to achieve a greater or lesser spring biasing of the rim member 16, as desired.

The front coil 30 is preferably formed at or near the midpoint of a single spring metal wire strand as shown in FIG. 6a. The rear coil 32 is formed by a combination of the free ends of the wire strand, with three (3) loops being formed on the first free end of the strand and two (2) loops being formed on the second free end of the strand. The loops formed in the first and second ends of the strand are then juxtapositioned in the manner shown in FIG. 6 to form, in combination, the five (5) loop front coil 32 of the preferred rim member 16a.

The tips of the free ends of the wire strand are turned inwardly to eliminate sharp protrusions as shown in FIGS. 6b and 7. The juxtapositioned free ends of the wire strand are affixed together to form a substantially unitary tongue member upon which the grasping member 18a may be mounted or formed. As shown in FIG. 6, an attachment apparatus, such as a crimp clip 33, may be utilized to join the free ends of the wire strand. Alternatively, as shown in FIG. 7, the free ends of the wire strand may be twisted or twined about one another to affix the free ends of the wire strand directly to one another without the use of a separate crimp member 33 or other attachment apparatus.

In the preferred embodiment shown, the rim member 16a is formed of stainless steel spring wire having an outer diameter of 0.015–0.025 inches and preferably approximately 0.020 inches. An optional plastic coating or covering 21, such as a cylindrical polyethylene covering, may be disposed on the outer surface of the wire 17. The disposition of such plastic coating or covering 21 on the outer surface of wire 17 serves (a) deter or prevent the wire 17 from cutting through the body of the containment sac body 15 and/or (b) to facilitate heat or adhesive sealing of the rim member 16a to the mouth of the sac body 15 such that the containment sac 15 will remain evenly distributed about the rim member 16a without regionalized puckering or pleating of the sac body 15 as may occur if a bare wire rim member 16 were freely disposed within the upper lip of the containment sac 15, without heat sealing or other attachment thereto. Such puckering or pleating of the sac body may occur as the containment sac 14 is being withdrawn into the introducer lumen 13.

In a presently preferred construction, the containment sac 15 may be formed of one or more layers of transparent plastic film. The upper portion of the containment sac 15 may be folded over the rim member 16a and heat or adhesive sealed to itself, thereby forming an enclosed internal channel 34 about the periphery of the opening or mouth of the sac 15. The rim member 16 is disposed within channel 37 and may be heat or adhesive sealed to the surrounding surfaces of the containment sac body 15. In instances where the rim member 16a is provided with the optional plastic cover or coating 21, such plastic cover or coating 21 may be directly heat fused to the adjacent surface of the containment sac 15.

An optional plastic reinforcement tape 36 may be positioned around the rear coil 32 and affixed to adjacent portions of the containment sac body 15 to reinforce the containment sac body 15 in the region of the sac body 15 wherefrom the free ends of the rim member 16 protrude. Such reinforcement tape 36 may comprise a strip of polyethylene tape which is heat or adhesive sealed to the surface of the containment sac 15, thereby accomplishing the desired reinforcement of the containment sac body 15 in the area immediately surrounding the opening through which the free ends of the rim member 16 pass. The reinforcement tape 36 is sized and positioned on the containment sac body 15 to distribute the pull forces over a portion of the sac body 15 and to reduce concentration of such forces on the rim member 16.

Figures 12A, 12B, 12C, 12D, 13A:
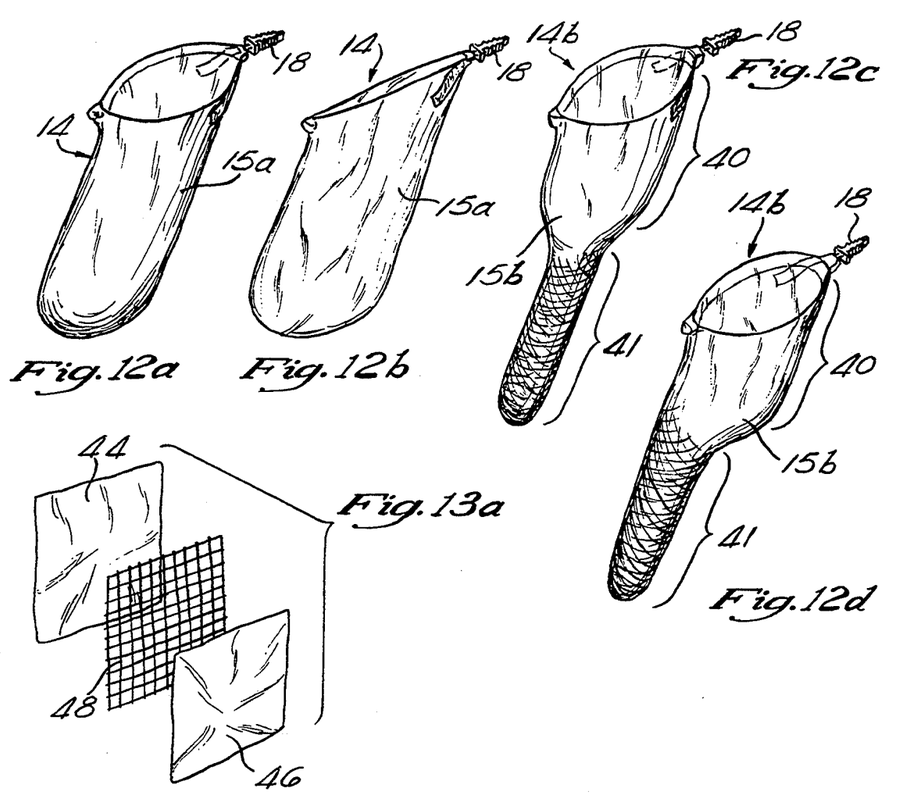

The containment sac 15 may be formed in many different sizes and configurations, depending on the intended application and use of the device 10. As shown in FIGS. 12a and 12b, one embodiment of the containment sac comprises a sac body 15a in the form of a pouch of relatively constant diameter. Alternatively, as shown in FIGS. 12c and 12d, the sac body 15b may comprise a top portion 40 of relatively large diameter and a bottom portion 41 of relatively small diameter.

The alternative configuration of the containment sac shown in FIGS. 12c and 12d serves to define upper and lower regions within the sac body 15b such that relatively large pieces of matter will remain in the larger sized upper body portion 40 while relatively small pieces of matter will be allowed to fall into the relatively small size lower body portion 41. The lower body portion 41 may be specifically sized such that the diameter of the lower body portion 41 is no greater than the size of the opening or incision through which the containment sac 14 is to be extracted. Thus, any matter which is sufficiently small to fit into the lower body portion 41 of the containment sac body 15b will be sufficiently small to be extracted through the opening or incision without the need for further grinding or debulking thereof. Furthermore, particles of relatively small matter which tend to aggregate or co-here to one another may have the tendency to form a substantially solid mass during residence within the sac 14. The specific sizing of the lower body portion 41 may serve to insure that small particles which have passed into such lower body portion 41 will aggregate in a long, narrow mass capable of being extracted through the minimal access body incision, as opposed to a larger diameter mass which may be unextractable through such minimal access body incision.

On the other hand, material which remains within the relatively large upper body portion 40 of the containment sac body 15b will likely require liquidization, grinding, or debulking before the containment sac body 15b may be extracted through the desired incision or body opening. Toward that end, a separate grinding or debulking instrument, such as that described in U.S. patent application Ser. No. 07/639,494, entitled METHOD AND DEVICE FOR INTRACORPOREAL LIQUIDIZATION OF TISSUE AND/OR FRAGMENTATION OF CALCULI DURING ENDOSCOPIC SURGICAL PROCEDURES, may be inserted into the upper body portion 40 of the containment sac body 15b and utilized to grind, liquidize, debulk, and/or aspirate matter from the upper body portion 40 of the containment sac 15b prior to extraction and removal of the containment sac body 15b from the body cavity. The smaller material disposed within the lower body 41 of the containment sac 15b may then be pulled directly through the incision or opening without the necessity of further grinding, liquidizing, debulking, or aspirating such material.

The containment sac body 15 may be comprised of any suitable material and, preferably, is formed of transparent plastic sheet, such as polyethylene film. Additionally, the containment sac 14 and more particularly the containment sac body 15, may include a quantity of lubricant disposed thereon which is preferably selected from the group consisting essentially of glycerin and silicone. In some embodiments, all or a portion of the containment sac body 15a may be reinforced by way of fibers, strands, or other reinforcing members disposed within the body of the containment sac 15b. In particular, as shown in FIG. 13, some or all of the containment sac body 15 may comprise an inner layer 44 and an outer layer 46 of transparent plastic film with a layer of reinforcing fibers 48 disposed therebetween.

In embodiments where the containment sac 14 is formed of multiple layers of material, each such layer may be formed of different types of material to optimize the specific function of each such layer. For example, in some embodiments, the sac body 15 may comprise an inner layer of a plastic material having relatively high strength and tear resistance in laminar juxtaposition to an outer plastic film layer, which has lower strength and tear resistance but which is more readily heat fusible or heat sealable. An example of such construction is a sac body 15 having an inner layer formed of nylon film and an outer layer formed of a more readily heat sealable polyethylene film.

The inner 44 and outer 46 plastic film layers may be heat fused in juxtaposition to one another so as to form a sandwich-like composite with the reinforcing material 48 disposed therein. An example of reinforcing material 48 which may be employed is a grid formed of fabricated polyethylene strips available commercially as CALAF® fabric, Amoco Nisseki Calif, INC., Suite 1400, 90075 Parkway, Atlanta, Ga. 30339.

As shown in FIGS. 12c and 12d, the reinforcing layer 48 may be combined to a specific portion of the containment sac body 15b such as the lower body portion 41 shown in FIGS. 12c and 12d. Such regionalized reinforcement of the containment sac body 15b will prevent the sac body 15b from stretching or tearing as it is pulled through a relatively small incision or laparoscopic portal.

Figure 13B:
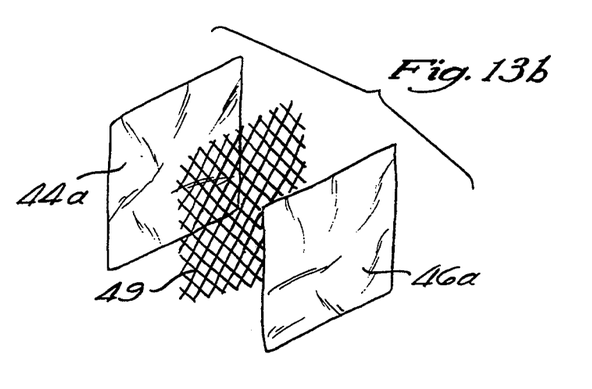
FIG. 13 is an exploded view of a portion of a containment sac of the present invention having an optional multi-layer reinforced construction.

Other types of fibers or reinforcing members may also be employed. For example, as shown in FIG. 13B, an expandable metal foil or expandable metal or plastic mesh 49 may be positioned between the inner 44A and outer 46A film layers. One example of such expandable foil or mesh 49 is that which is commercially available as MICROGRID ™ Precision Expanded Foil, Delker Corporation, 16 Commercial Street, P.O. Box 427, Branford, Conn. 06405. Such expandable foil or mesh 49 will serve to impart strength and tear resistance to the composite structure of the sac body 15. Additionally, such expandable metal foil or mesh may be incorporated for the added purpose of endowing the sac body 15 with the added capability of being selectably expanded by way of a balloon or other pressure exerting expander tool or member. Such capability of selective expansion/contraction will permit the operator to selectively expand all or a portion of the sac body 15 after the sac has been inserted into the body cavity. One embodiment of an invention incorporating such expandable metal foil insert is described in more detail herebelow.

B. A Selectively Expandable Embodiment of the Containment Sac

Figures 15A, 15B, 16, 17:
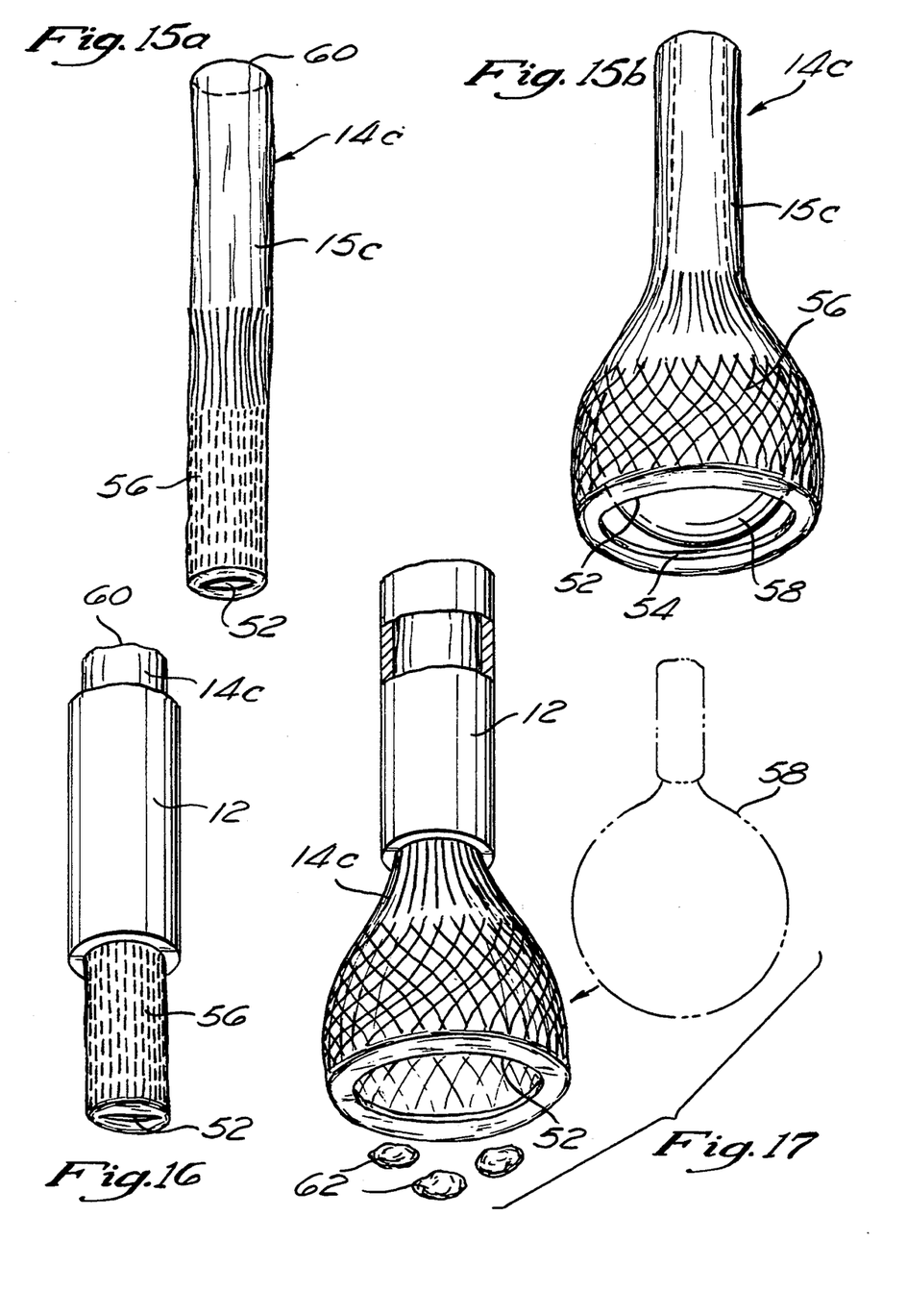
FIG. 15a is a perspective view of an expandable embodiment of a containment sac of the present invention in a "collapsed" configuration.
FIG. 15b is a perspective view of an expandable embodiment of a containment sac of the present invention in an "expanded" configuration.
FIG. 16 is a perspective view of an expandable containment sac of the present invention partially inserted through a tubular trocar or introducer in its "collapsed" configuration.
FIG. 17 is a perspective view of an expandable containment sac of the present invention which has been inserted through a tubular trocar or introducer and which has been expanded to an "expanded" configuration.

In some embodiments of the invention, the containment sac 14c may be specifically constructed and configured to be selectively expandable by way of an expansion tool or balloon 58. An example of such embodiment is shown in FIGS. 15-17. Specifically, such embodiment comprises a containment sac 14c having an elongate sac body 15c with a sealable opening 52 formed in the bottom end thereof. Such sealable opening may incorporate any suitable type of closure apparatus 54 such as a zipper, tongue-in-groove plastic compressible closure mechanism, or other means for forming a substantially liquid-tight seal of the bottom opening 52 of the containment sac 14c. A cylindrical segment of expandable metal foil 56 is positioned within at least the bottom of the containment sac 14c as shown. To permit expansion of such expandable metal foil 56, the bottom portion of the containment sac 14 will be formed of one or more layers of film or sheet material which is sufficiently elastic, or which incorporates sufficient slack to permit the expandable metal foil 56 to be expanded from its collapsed configuration (FIG. 15a) to its expanded configuration (FIG. 15b). Such expansion may be accomplished by insertion of a rigid expansion tool or by inflation of an expander balloon 58 within the interior of the sac 14c.

As shown in FIGS. 16 and 17, the expandable embodiment of the containment sac 14c may be utilized in conjunction with any suitable type of tubular trocar or introducer sheath. Such expandable containment sac 14c may be initially disposed in its "collapsed" configuration (FIG. 16) and thereby inserted through the tubular trocar or introducer sheath 12 to a point where a portion of the containment sac 14c extends out of and beyond the distal end D of the trocar or sheath 12. The expandable metal foil 56 is located within the portion of the containment sac 14c which extends out of and beyond the distal end D of the trocar or introducer sheath 12.

A suitable expansion instrument or balloon is then inserted through the top opening 60 of the containment sac 14c and is utilized to expand the expandable metal foil 56 to an expanded configuration (FIG. 17) with the bottom portion of the containment sac 14c in such "expanded" configuration, the desired organ tissue or particles of matter 62 may be inserted through the bottom opening 52 of the containment sac 14c. Thereafter, the closure apparatus 54 is utilized to form a substantially liquid tight seal of the bottom opening 52 of the containment sac 14c.

After the bottom opening 52 of the containment sac 14c has been closed, a liquidizing or debulking instrument may be inserted through the top opening 60 of the containment sac and utilized to liquidize, debulk and/or aspirate the matter 62 from the interior of the containment sac.

After the matter 62 has been debulked and/or aspirated from the interior of the containment sac, the containment sac 14c may be pulled in a proximal direction such that the pressure exerted by the walls of the trocar or sheath 12 will cause the expandable metal foil 56 to once again collapse as it passes through the lumen of the trocar or sheath 12 and is thereby extracted from the body.

Figures 18, 19, 20, 21:
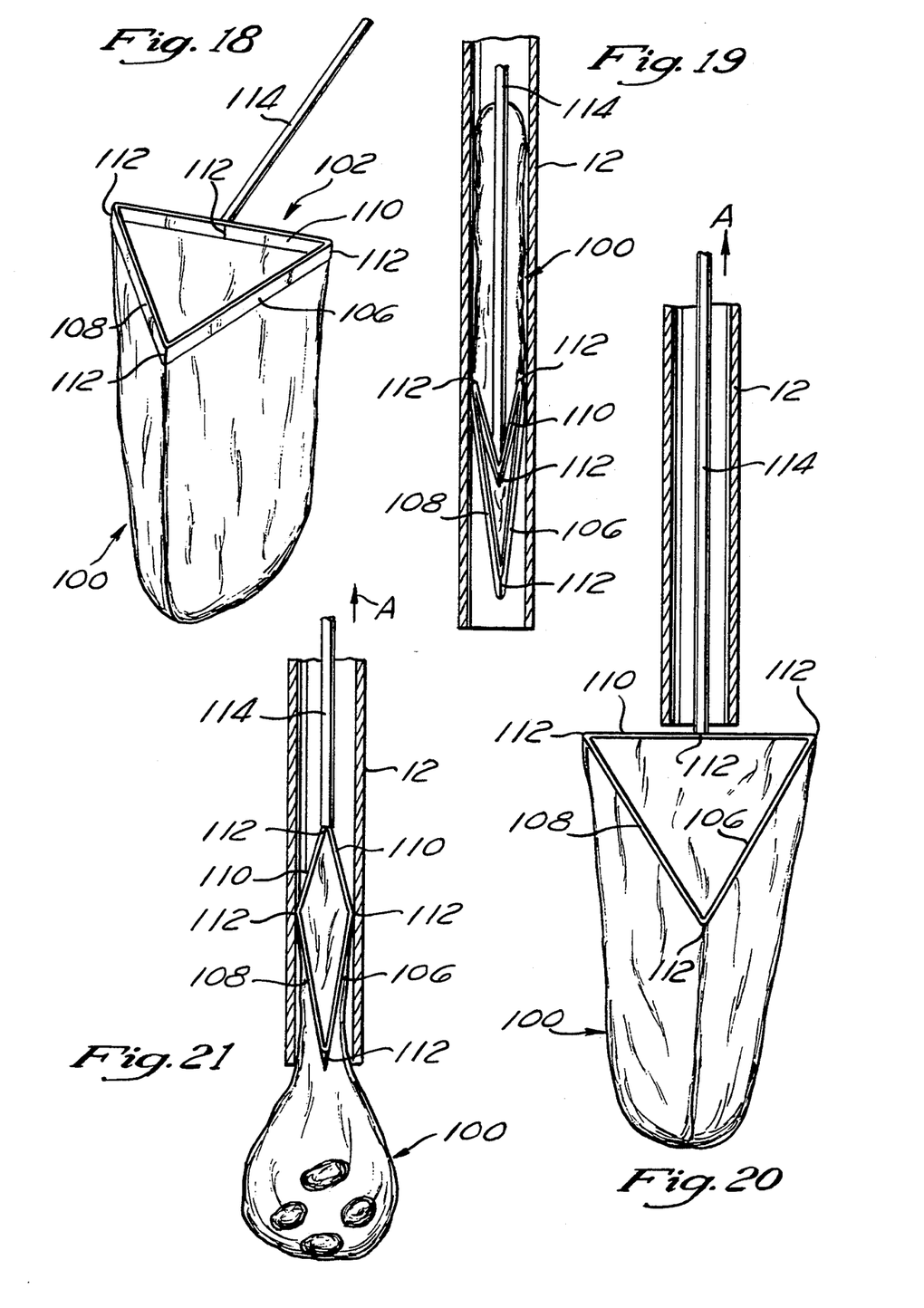
FIG. 18 is a perspective view of an alternative embodiment of the containment sac which may be utilized in conjunction with the present invention.
FIG. 19 is a cross-sectional view illustrating the containment sac shown in FIG. 18 as initially stored within the introducer sheet of the present invention.
FIG. 20 is a perspective view illustrating the containment sac shown in FIG. 18 in a deployed state.
FIG. 21 is a cross-sectional view illustrating the upper portion of the containment sac shown in FIG. 18 as being partially retracted within the introducer sheath.

C. An Alternative Embodiment of the Containment Sac Incorporating a Hinged Rim Member Referring now to FIGS. 18-21, illustrated is a containment sac 100 which may be utilized in conjunction with the present invention as an alternative to the containment sac previously shown and described. As seen in FIG. 18, containment sac 100 includes a rim number 102 defining an entrance 104 thereto. Importantly, like rim number 16 used in conjunction with containment sac 14, the rim number 102 of this embodiment is adapted to provide access to the interior of containment sac 100, i.e. maintain entrance 104 in an open orientation, when containment sac 100 is deployed from the introducer sheath 12. In the alternative embodiments, rim number 102 is preferably formed from a single plastic strip which assumes a generally triangular configuration when the containment sac 100 is fully deployed from the introducer sheath 12. In this respect, when the containment sac 100 is deployed, the rim number 102 defines a first segment 106, second segment 108 and third segment 110. Importantly, rim number 102 is formed so as to include living hinges 112 in each of the three corners defined by the segments 106, 108, 110. An additional living hinge 112 is included in the center portion of the third segment 110 for reasons which will be discussed below. Attached to and extending from the third segment 110 in close proximity to the living hinge 112 form therein is an elongate tether 114.

Referring now to FIG. 19, when containment sac 100 is initially stored within the introducer sheath 12, the rim member 102 assumes a collapsed orientation whereby the third segment 110 is bent inwardly toward the living hinge 112 disposed between the first segment 106 and second segment 108. The containment sac 100 is deployed from the distal tip of the introducer sheath 112 via the utilization of a plunger or similar instrument. As seen in FIG. 20, once the containment sac 110 is fully deployed from the introducer sheath 12, the tether 114 is drawn in the direction shown by the arrow A so as to cause the opposed ends of the third segment 110 to come into abutting contact with the distal tip of introducer sheath 12. After such contact occurs, the tether 114 is further drawn such that the third segment 110 bends outwardly away from the living hinge 112 disposed between first segment 106 and second segment 108 so as to assume a generally horizontal orientation. As will be recognized, when third segment 110 is drawn via tether 114 to the horizontal orientation, the rim member 102 is caused to fully open the entrance 104 to the containment sac 100. Thereafter, an organ or other tissue may be inserted into the containment sac 100 via entrance 104.

Referring now to FIG. 21, after the organ or other tissue has been inserted into the containment sac 100, the tether 114 is further drawn in the direction designated by the arrow A. Due to the abutting contact of the opposed portions of the third segment 110 against the distal tip of introducer sheath 112, further pulling the tether 114 in this manner will actuate the living hinge 112 disposed in third segment 110 thereby causing the third segment 110 to bend outwardly away from the living hinge 112 disposed between the first segment 106 and second segment 108. As will be recognized, collapsing the rim member 102 in this manner allows the rim member 102 as well as the upper portion of the containment sac 100 to be drawn into the distal end of the introducer sheath 12. Thereafter, the upper-end of the containment sac 100 may be exteriorized in the same manner previously described so that subsequent operations may be conducted to the contents of the containment sac 100. In the preferred embodiment, the rim member 102 is formed of a plastic strip made of polyethylene, though other materials may be utilized as an alternative. Additionally, the living hinges 112 are preferably formed in the rim member 102 via selective cuts placed into the polyethylene plastic strip. It will be recognized that the rim member 102 may be formed from individual segments joined in a manner so as to form the four hinges previously described. Additionally, it will further be recognized that the containment sac 100 may be utilized independently of the introducer sheath 12 and actuated to an open position by the abutment of the opposed ends of the third segment 110 against the inner wall of the abdominal cavity with the tether 114 being drawn upwardly through the access incision to cause the entrance 104 to assume the open position.

D. Method of Using A Device of the Present Invention

The presently preferred embodiment of the invention described herein may be utilized to contain and remove tissue or other matter from a body cavity, in accordance with the diagrams set forth as FIGS. 14a–14f.

Figures 14A, 14B, 14C, 14D:
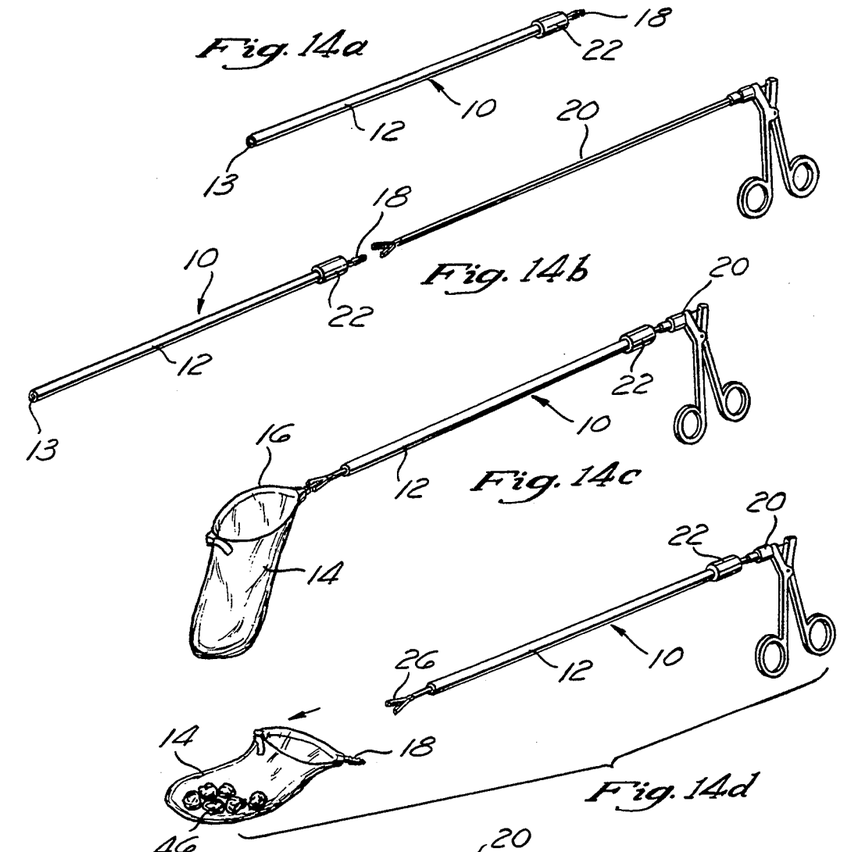
FIGS. 14a–14f is a step-wise schematic illustration of a presently preferred method of operating a device of the present invention.

As shown in FIG. 14a, the device 10 is initially disposed in its "pre-operative" configuration whereby the containment sac 14 is fully disposed within the lumen 13 of the introducer sheath 12 and the gripping member 18 is deployed out of the proximal end of the device 10.

After the distal end of the introducer sheath 12 has been inserted into the desired body cavity, a forcep/grasper instrument 20 is utilized to grasp the grasping member 18 as illustrated in FIG. 14b.

Thereafter, the forcep/grasper instrument 20 is advanced in a distal direction to a point where the containment sac 14 has been fully expelled out of the distal end of the introducer sheath 12. Upon expulsion of the containment sac 14 from the distal end of the introducer sheath 12, the biased rim member 16 will cause the mouth of the containment sac body 15 to assume an open configuration.

Figures 14E, 14F:
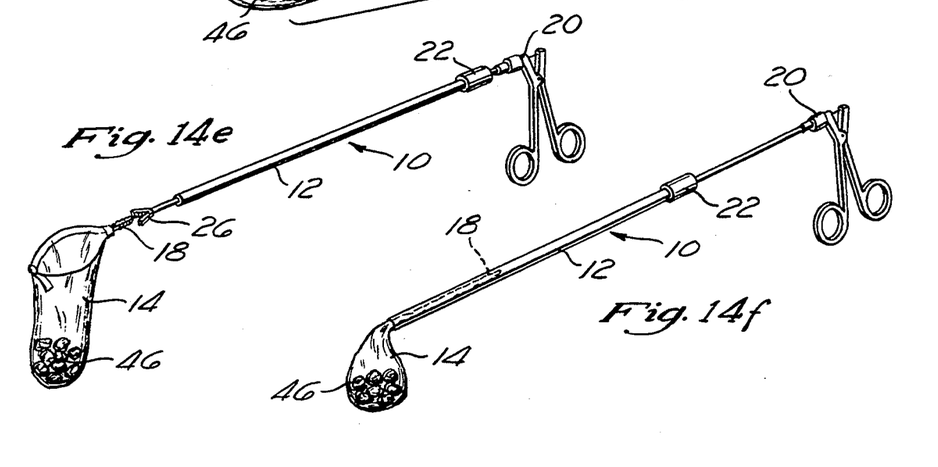

Thereafter, as shown in FIG. 14b, the jaws 26 of the forcep/grasper instrument 20 may be relaxed, thereby releasing the containment sac 14. Attendant instruments are then utilized to manipulate and move the containment sac 14 to a desired location within the body cavity and the organ/calculi or other matter 46 to be removed is deposited within the containment sac 14. Thereafter, the containment sac 14 is returned to a position near the distal end of the introducer sheath 12 and the jaws 26 of the forcep/grasper instrument 20 are once again utilized to engage and hold the grasping member 18 of the containment sac 14 as shown in FIG. 14e.

After the jaws 26 of the forcep/grasping instrument 20 have re-engaged the grasping member 18 of the containment sac 14, the forcep/grasper instrument 20 is retracted in a distal direction, thereby pulling the rim portion of the containment sac 14 into the lumen 13 of the introducer sheath 12. The containment sac 14 is typically withdrawn to a point where the rim member 16 is fully within the lumen 13 of the introducer sheath 12. This is shown in FIG. 14f.

After the rim portion of the containment sac 14 has been withdrawn into the introducer sheath 12 and the forcep/grasper instrument are simultaneously extracted from the body and removed, thereby leaving the top portion of the containment sac 14 exteriorized from the body while the matter containing lower portion of the containment sac 14 remains within the body cavity. If the matter 46 within the containment sac 14 is too large to permit extraction through the desired incision, a separate debulking or liquidizing instrument may be utilized to liquidize, grind, debulk, and/or aspirate the matter 46 from the containment sac 14. Thereafter, the containment sac 14 is removed from the body cavity and the minimal access incision is closed.

The device 10 described herein is but one example of an embodiment of the present invention. Similarly, the methodology described herein is but one example of an operative procedure that may be carried out using the device of the present invention. It will be appreciated that other embodiments of the invention, and other method of use, may be employed, all of which are within the intended scope of the present patent application.

The foregoing description of the preferred embodiments and examples of the invention are not intended to limit the invention in any way. In fact, by applying current or future knowledge, those skilled in the art will recognize numerous modifications, substitutions, deletions, or alterations which may be made to the above-described embodiments and examples without departing from the spirit and scope of the present invention. It is intended that all such modifications, substitutions, deletions, or alterations be included within the scope of the following claims, and the equivalents thereof.

What is claimed is:

1. A device usable, in combination with a standard forcep/grasper instrument, to deploy a surgical containment sac within a body cavity and to subsequently retrieve said containment sac from said body cavity, said device comprising:
    a tubular introducer sheath having a distal end, a proximal end, and a hollow lumen extending longitudinal therethrough;
    a flexible containment sac comprising:
        (a) a flexible sac body having at least one opening thereinto; and
        (b) a rigid grasping member connected to said sac body, said grasping member being sized and configured to be graspable by said standard forcep/grasper instrument;
    said containment sac and said tubular introducer sheath being sized and configured relative to one another so as to permit said containment sac to be alternately deployable in:
        (a) a first "pre-operative" position wherein said containment sac body is fully disposed within a lumen of said introducer sheath with said grasping member extending at least partially out of the proximal end of said introducer sheath;
        (b) a second "deployed" position whereby said containment sac is expelled out of the distal end of said introducer sheath; and
        (c) a third "retraction" position whereby a portion of said containment sac is withdrawn into the lumen of the introducer sheath, while a portion of said containment sac remains disposed beyond the distal end of said introducer sheath.

2. The device of claim 1 further comprising:
    a valving cap member positioned on the proximal end of said introducer sheath, said valving cap member comprising a transverse diaphragm positioned over the proximal end of said introducer sheath, a slit being formed in said transverse diaphragm to permit passage of said forcep/grasper instrument therethrough.

3. The device of claim 1 wherein said introducer sheath comprises a rigid plastic tube.

4. The device of claim 1 wherein said containment sac further comprises:
    a rim member disposed about the opening of said containment sac body.

5. The device of claim 4 wherein said rim member is formed of spring metal wire.

6. The device of claim 5 wherein at least one coil is formed in said spring metal wire rim member to cause said rim member to urge said containment sac to an open configuration.

7. The device of claim 6 wherein said at least one coil comprises first and second coils formed at separate locations on said rim member.

8. The device of claim 7 wherein each of said first and second coils comprises five loops of spring metal wire positioned in adjacent juxtaposition to form said coils.

9. The device of claim 4 wherein said rim member is formed of spring metal wire having a plastic cover disposed thereon.

10. The device of claim 6 wherein said plastic cover is fused to said containment sac body.

11. The device of claim 10 wherein said plastic cover is heat-sealed to said containment sac body.

12. The device of claim 4 wherein said grasping member is connected to said rim member.

13. The device of claim 4 wherein said rim member is formed of spring metal wire.

14. The device of claim 4 wherein said rim member is formed of spring metal wire having a plastic cover disposed thereon.

15. The device of claim 14 wherein said plastic cover is fused to said containment sac body.

16. The device of claim 15 wherein said plastic cover is heat sealed to said containment sac body.

17. The device of claim 14 wherein at least one coil is formed in said spring metal wire rim member to cause said rim member to urge said containment sac to an open configuration.

18. The containment sac of claim 17 wherein said at least one coil comprises first and second coils formed at separate locations on said rim member.

19. The device of claim 18 wherein each of said first and second coils comprises five loops of spring metal wire positioned in adjacent juxtaposition to form said coils.

20. The device of claim 1 wherein said introducer sheath has an outer diameter of approximately 1 cm.

21. The device of claim 1 wherein said containment sac body comprises transparent plastic film.

22. The device of claim 21 wherein said containment sac body comprises at least one layer of transparent plastic film in juxtaposition to at least one layer of reinforcing material.

23. The device of claim 22 wherein said at least one layer of reinforcing material comprises a plurality of plastic fibers arranged in a grid pattern.

24. The device of claim 22 wherein said reinforcing material comprises a plurality of cut plastic strips arranged in a grid pattern.

25. The device of claim 24 wherein said containment sac body comprises at least one layer of transparent plastic film and wherein said lower portion of said containment sac body further comprises reinforcing members to enhance the strength of said plastic film.

26. The device of claim 22 wherein said reinforcing material comprises expandable mesh.

27. The device of claim 1 wherein said containment sac body comprises first and second layers of transparent plastic film.

28. The device of claim 1 wherein said flexible sac body comprises an upper portion and a lower portion, the lower portion of said sac body being of smaller cross-sectional dimension than the upper portion of said sac body such that pieces of matter having cross-sectional dimensions greater than the cross-sectional dimension of said lower portions will be prevented from entering said lower portion and will be retained in the upper portion of said sac body.

29. The device of claim 28 wherein said reinforcing members comprise a plurality of plastic fibers arranged in a grid pattern.

30. The device of claim 28 wherein said reinforcing members comprise a plurality of cut plastic strips arranged in a grid pattern.

31. The device of claim 28 wherein said reinforcing members comprise expandable mesh.

32. The device of claim 1 wherein said sac comprises a pouch of approximately 2.5 inches in diameter and approximately 5 inches in length.

33. The device of claim 1 wherein said sac is formed of materials selected from the group consisting of:
   polyethylene;
   nylon; and
   vinyl.

34. The device of claim 1 further comprising a quantity of lubricant disposed on said containment sac.

35. The device of claim 34 wherein said lubricant is selected from the group consisting essentially of:
   glycerin; and
   silicone.

36. The device of claim 1 wherein said introducer is approximately 3-20 inches in length.

37. The device of claim 1 wherein said introducer is sized to be insertable through a standard laparoscopy portal.

38. The device of claim 1 wherein said grasping member comprises a body having a plurality of serrated teeth formed thereon.

39. The device of claim 1 wherein said grasping member comprises a rigid body having a front end and a rear end and wherein a flange member is formed on the front end of said rigid body to facilitate grasping of said grasping member by a standard forcep/grasping instrument.

40. A surgical containment sac insertable into a body cavity through a minimal access incision, said containment sac comprising:
   (a) a flexible sac body having at least one opening thereinto;
   (b) a rigid grasping member connected to said sac body, said grasping member being sized and configured to be graspable by a standard forcep/grasper instrument;
   (c) said containment sac being sized and configured so as to be collapsible to a configuration which will pass through a minimal access incision of approximately one centimeter in length.

41. The containment sac of claim 40 further comprising:
   a rim member disposed about the opening of said containment sac body.

42. The containment sac of claim 41 wherein said grasping member is connected to said rim member.

43. The containment sac of claim 40 wherein said containment sac body comprises transparent plastic film.

44. The containment sac of claim 40 wherein said containment sac body comprises first and second layers of transparent plastic film.

45. The containment sac of claim 40 wherein said containment sac body comprises at least one layer of transparent plastic film in juxtaposition to at least one layer of reinforcing material.

46. The containment sac of claim 45 wherein said layer of reinforcing material comprises a plurality of plastic fibers arranged in a grid pattern.

47. The containment sac of claim 45 wherein said reinforcing material comprises a plurality of cut plastic strips arranged in a grid pattern.

48. The containment sac of claim 45 wherein said reinforcing material comprises expandable mesh.

49. The containment sac of claim 40 wherein said flexible sac body comprises an upper portion and a lower portion, the lower portion of said sac body being of smaller cross-sectional dimension than the upper portion of said sac body such that pieces of matter having cross-sectional dimensions greater than the cross-sectional dimension of said lower portions will be prevented from entering said lower portion and will be retained in the upper portion of said sac body.

50. The containment sac of claim 49 wherein said containment sac body comprises at least one layer of transparent plastic film and wherein said lower portion of said containment sac body further comprises a reinforcing material to enhance the strength of said plastic film.

51. The containment sac of claim 50 wherein said reinforcing material comprises a plurality of plastic fibers arranged in a grid pattern.

52. The containment sac of claim 50 wherein said reinforcing material comprises a plurality of cut plastic strips arranged in a grid pattern.

53. The containment sac of claim 50 wherein said reinforcing material comprises expandable mesh.

54. The containment sac of claim 40 wherein said sac comprises a pouch of approximately 2.5 inches in diameter and approximately 5 inches in length.

55. The containment sac of claim 40 wherein said sac is formed of materials selected from the group consisting of:
   polyethylene;
   nylon; and
   vinyl.

56. The containment sac of claim 40 further comprising a quantity of lubricant disposed on said containment sac.

57. The containment sac of claim 56 wherein said lubricant is selected from the group consisting essentially of:
   glycerin; and
   silicone.

58. The containment sac of claim 40 wherein said grasping member comprises a body having a plurality of serrated teeth formed thereon.

59. The containment sac of claim 40 therein said grasping member comprises a rigid body having a front end and a rear end and wherein a flange member is formed on the front end of said rigid body to facilitate grasping of said grasping member by a standard forcep/grasping instrument.

* * * * *